(12) United States Patent
McGlone (10) Patent No.: US 11,617,715 B2
(45) Date of Patent: *Apr. 4, 2023

(54) METHODS AND COMPOSITIONS FOR MODIFYING THE BEHAVIOR OF ANIMALS

(71) Applicant: Texas Tech University System, Lubbock, TX (US)

(72) Inventor: John J. McGlone, Southland, TX (US)

(73) Assignee: TEXAS TECH UNIVERSITY SYSTEM, Lubbock, TX (US)

( * ) Notice: Subject to any disclaimer, the term of this patent is extended or adjusted under 35 U.S.C. 154(b) by 338 days.

This patent is subject to a terminal disclaimer.

(21) Appl. No.: 16/322,701

(22) PCT Filed: Aug. 1, 2017

(86) PCT No.: PCT/US2017/044830
§ 371 (c)(1),
(2) Date: Feb. 1, 2019

(87) PCT Pub. No.: WO2018/026772
PCT Pub. Date: Feb. 8, 2018

(65) Prior Publication Data
US 2019/0269615 A1    Sep. 5, 2019

Related U.S. Application Data

(60) Provisional application No. 62/369,853, filed on Aug. 2, 2016.

(51) Int. Cl.
| | | |
|---|---|---|
| A61K 31/47 | (2006.01) | |
| A61K 47/06 | (2006.01) | |
| A61K 9/12 | (2006.01) | |
| A61K 9/00 | (2006.01) | |
| A61K 47/10 | (2017.01) | |

(52) U.S. Cl.
CPC .............. *A61K 9/0073* (2013.01); *A61K 9/12* (2013.01); *A61K 31/47* (2013.01); *A61K 47/06* (2013.01); *A61K 47/10* (2013.01)

(58) Field of Classification Search
None
See application file for complete search history.

(56) References Cited

U.S. PATENT DOCUMENTS

| | | |
|---|---|---|
| 4,263,873 A | 4/1981 | Christianson |
| 5,415,131 A | 5/1995 | Dodman |
| 9,044,395 B2 | 6/2015 | McGlone et al. |
| 9,480,689 B1 | 11/2016 | McGlone |
| 2005/0154008 A1 | 7/2005 | Cai et al. |
| 2006/0252738 A1 | 11/2006 | Avelino |
| 2008/0193387 A1* | 8/2008 | De Wolff ............... A61K 36/53 424/47 |
| 2009/0203735 A1* | 8/2009 | Corfas ..................... A61K 9/20 514/313 |
| 2011/0150822 A1 | 6/2011 | Nouvel et al. |
| 2012/0318205 A1 | 12/2012 | Kuras et al. |
| 2013/0072570 A1 | 3/2013 | McGlone et al. |
| 2013/0156839 A1* | 6/2013 | Messina ................ A01N 61/02 424/410 |
| 2013/0210927 A1 | 8/2013 | Nouvel et al. |
| 2014/0000526 A1 | 1/2014 | Kuras et al. |
| 2015/0366878 A1 | 12/2015 | Levin et al. |
| 2016/0106058 A1 | 4/2016 | McGlone et al. |

OTHER PUBLICATIONS

Eisner, "Defensive Production of Quinoline by a Phasmid Insect (*Oreophoetes peruana*)", The Journal of Experimental Biology 200, 2493-2500, 1997 (Year: 1997).*

Cheng, "the Friedländer Synthesis of Quinolines", Organic Reactions, vol. 28, 1982 (Year: 1982).*

* cited by examiner

*Primary Examiner* — Robert T. Crow
*Assistant Examiner* — John P Nguyen
(74) *Attorney, Agent, or Firm* — Loza & Loza LLP; Kevin L. Soules (57) ABSTRACT

A composition comprising Quinoline is described for the modification of undesirable or harmful behaviors or other behaviors or physiology in a variety of vertebrate species, as well as methods of using the compositions in vertebrates.

6 Claims, 4 Drawing Sheets

Quinoline. CAS Number 91-22-5

$C_9H_7N$ Molecular weight 129.16

FIG. 1

Properties

200

| | |
|---|---|
| Related Categories | Cell Biology, Ephedra sinica, Ligands and Metal Complex Precursors, Materials Science, Nutrition Research, More... |
| grade | reagent grade |
| vapor density | 4.5 (vs air) |
| vapor pressure | 0.07 mmHg ( 20 °C) |
| assay | 98% |
| autoignition temp. | 896 °F |
| refractive index | n20/D 1.625(lit.) |
| bp | 113-114 °C/11 mmHg(lit.) |
| | 237 °C(lit.) |
| mp | −17−13 °C(lit.) |
| density | 1.093 g/mL at 25 °C(lit.) |
| Gene Information | human ... CYP2D6(1565) |

Results of three studies on the efficacy of Quinoline to reduce dog jumping and barking.

| | | 1 minute after treatment | |
|---|---|---|---|
| Study 1 | Number dogs | % Jumping reduced | % Barking reduced |
| Nothing | 20 | 55% | 45% |
| Control | 20 | 65% | 85% |
| Quinoline | 10 | 90% | 80% |
| | | | |
| Study 2 | | | |
| Quinoline | 10 | 90% | 100% |
| | | | |
| Study 3 | | | |
| Quinoline | 13 | 85% | 77% |
| Androstenone | 15 | 87% | 80% |

METHODS AND COMPOSITIONS FOR MODIFYING THE BEHAVIOR OF ANIMALS

CROSS REFERENCE TO RELATED APPLICATIONS

This application is the US national phase of International Application No. PCT/US2017/044830, filed on Aug. 1, 2017 under the PCT (Patent Cooperation Treaty), and claims priority to U.S. Provisional Patent Application No. 62/369,853, filed Aug. 2, 2016. The contents of these applications are incorporated herein by reference in their entirety.

TECHNICAL FIELD

Embodiments are generally related to the field of animal behavior and the use of pheromones and, in particular, Quinoline compositions. More particularly, the present disclosure is concerned with the use of the pheromone Quinoline to produce, or otherwise affect, behavior (such as a calming or behavioral-altering effect) in a variety of vertebrate species; for example, in dogs, cats, snakes, birds, or horses.

BACKGROUND

Pheromones are chemicals released by living organisms that send information to other organisms of the same species via scent. Pheromones are released in response to stress, alarm, danger, sexual fertility, and in other behavioral contexts. Pheromones, by definition, and according to evolutionary theory, are species-specific; that is, they are effective in eliciting an innate response only in members of the same species.

Chemicals that provide interspecies communication are called allelochemicals. Some compounds are known to be a pheromone in one species, but have been observed to have strong behavioral effects in other species. For example, chemicals produced and released by one species that affect the behavior or physiology of another species to the benefit of the originator, but not the receiver, are known in the art as allomones (See Gras Switz, T. R. and G. R. Jones (2002). "Chemical Ecology". Encyclopedia of Life Sciences. John Wiley & Sons, Ltd. doi:10.1038/npg.els 0.0001716). The production of allomones in natural environments has been mainly observed in plant species, which utilize allomones, for example, to protect plants against insect herbivores.

A kairomone is another known allelochemical. It is emitted by one species and benefits another species, but does not benefit, and often harms, the emitter. The production of kairomones in natural environments has been mainly observed in insect species. For example, the Ponderosa Pine tree produces a terpene called myrcene when the Western Pine Beetle damages the tree. The emission of this chemical then lures more beetles to the tree (See Wyatt, T. D. (2003), Pheromones and Animal Behavior: Communication by Smell and Taste, First Edition (Cambridge, UK: Cambridge University Press)).

A synomone is an allelochemical produced and released by one species that benefits both the emitter and receiver. For example, plants emit odors that work to attract bees. The bees are attracted to the plants to feed, and then the bees take the pollen to fertilize other plants/flowers.

Accordingly, the allelochemicals known in the art involve chemicals produced by one species having an effect on another species to the benefit and/or detriment of the emitting or receiving species.

Prior art methods used to stop barking/jumping/begging in a variety of animal species include shock collars, odor sprays, and loud noises, all of which work by startling or distracting the animal from engaging in the undesirable behavior. Animal appeasing pheromones, including synthetic compositions believed to replicate certain calming pheromones emitted by animals, have also been used in the art to treat certain behavioral problems in animals.

For example, certain pheromones such as Androstenone have been used for this purpose. Androstenone is a steroid found in a number of vertebrate species. Androstenone has also been found to alter the behavior of other vertebrate species, as disclosed in U.S. Pat. No. 9,044,395 titled "Pheromone compositions and their use to modify behavior in different vertebrate species." While Androstenone has been identified as one pheromone that may alter the behavior of vertebrates, it is believed that other compounds may have similar affects.

Accordingly, there is a need in the art for use of a pheromone to calm, sedate, reduce anxiety, or otherwise positively modify the behavior of a variety of vertebrate species, including the barking/jumping/begging syndrome exhibited by some dogs.

BRIEF SUMMARY

The following summary is provided to facilitate an understanding of some of the innovative features unique to the embodiments disclosed and is not intended to be a full description. A full appreciation of the various aspects of the embodiments can be gained by taking the entire specification, claims, drawings, and abstract as a whole.

Various objects and advantages of this use will become apparent from the following description taken in conjunction with the accompanying drawings which describe certain embodiments of this invention.

It is, therefore, one aspect of the disclosed embodiments to provide novel methods and compositions for the modification of behavior in vertebrate species comprising compounds that have been isolated from one vertebrate species, but have the effect of modifying the behavior in a different vertebrate species.

Specifically, in an aspect of the embodiments, certain pheromones such as Quinoline can be made into compounds and used as part of a method to modify the behavior of other animals. An INTEROMONE® is any naturally secreted or synthetically produced chemical emitted as a pheromone within one species, which, when isolated and administered to a member of a different vertebrate species, elicits a change in behavior or physiology of the different species, without the requirement of benefiting and/or harming the species from which the chemical is released.

The present embodiments describe the INTEROMONE® Quinoline and its use in various compositions to cause a modification of behavior in a variety of vertebrates, for example, dogs, horses, cats, snakes, and birds. Quinoline is an odorous pheromone isolated strictly from boar saliva. Quinoline offers a powerful effect roughly equivalent to that of Androstenone on other species, such as dogs, and has been observed to change dog behavior.

Embodiments disclosed herein can include other compositions as necessary or desired, depending on the form and intended use of the final product. Such compositions can include, but are not limited to, carriers such as water, alcohols, solvents, fragrances, coloring agents, preservatives, antioxidants, and the like. Examples of the resultant product include, but are not limited to, an aerosol or a spray.

Alternatively, the resultant product may be a diffuser, collar, spraying collar, foam, dip, wipe, cream, gel, lotion, or fabric garment.

In another embodiment, a method for modifying, or positively affecting, the behavior of a vertebrate comprises administering a composition comprising an INTEROMONE®, such as Quinoline, in an amount effective to affect the behavior of a particular vertebrate, wherein the vertebrate whose behavior is being modified is different than that from which the INTEROMONE® is emitted as a pheromone.

The aforementioned aspects and other objectives and advantages can now be achieved as described herein.

BRIEF DESCRIPTION OF THE FIGURES

The accompanying figures, in which like reference numerals refer to identical or functionally-similar elements throughout the separate views and which are incorporated in and form a part of the specification, further illustrate the embodiments and, together with the detailed description, serve to explain the embodiments disclosed herein.

DETAILED DESCRIPTION

The particular values and configurations discussed in the following non-limiting examples can be varied, and are cited merely to illustrate one or more embodiments and are not intended to limit the scope thereof.

Example embodiments will now be described more fully hereinafter with reference to the accompanying drawings, in which illustrative embodiments are shown. The embodiments disclosed herein can be embodied in many different forms and should not be construed as limited to the embodiments set forth herein; rather, these embodiments are provided so that this disclosure will be thorough and complete, and will fully convey the scope of the embodiments to those skilled in the art. Like numbers refer to like elements throughout.

As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Throughout the specification and claims, terms may have nuanced meanings suggested or implied in context beyond an explicitly stated meaning. Likewise, the phrase "in one embodiment" as used herein does not necessarily refer to the same embodiment, and the phrase "in another embodiment" as used herein does not necessarily refer to a different embodiment. It is intended, for example, that claimed subject matter include combinations of example embodiments in whole or in part.

In general, terminology may be understood, at least in part, from usage in context. For example, terms such as "and," "or," or "and/or" as used herein may include a variety of meanings that may depend, at least in part, upon the context in which such terms are used. Typically, "or" if used to associate a list, such as A, B, or C, is intended to mean A, B, and C, here used in the inclusive sense, as well as A, B, or C, here used in the exclusive sense. In addition, the term "one or more" as used herein, depending at least in part upon context, may be used to describe any feature, structure, or characteristic in a singular sense or may be used to describe combinations of features, structures or characteristics in a plural sense. Similarly, terms such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The particular values and configurations discussed in these non-limiting examples can be varied and are cited merely to illustrate at least one embodiment and are not intended to limit the scope thereof.

The broad term "INTEROMONE®" is used herein to refer to chemicals emitted as pheromones within one vertebrate species that influence the behavior or physiology of a different species without the requirement of benefiting and/or harming the emitter or receiving species (although an INTEROMONE® could benefit or harm the emitting or receiving species).

The embodiments disclosed herein are directed to the use of Quinoline in a composition as an INTEROMONE®. Quinoline is a pig pheromone found in boar saliva. It can be used in order to modify the behavior of different vertebrate species (such as, for example, dogs, cats, horses, frogs, snakes, birds, etc.). In certain embodiments, Quinoline has been formulated into a composition as an INTEROMONE® for administration to different species (such as, for example, a horse, dog, cat, and other vertebrates) in order to positively modify the behavior of members of the different species.

In certain embodiments, administration of Quinoline as an INTEROMONE® to dogs results in reducing unwanted activity, or positively modifying the behavior of dogs that exhibit anxious behaviors.

In an embodiment, a composition comprising an INTEROMONE® is disclosed, which is a chemical or compound related thereto emitted by one species and known to be a pheromone within that species to modify the behavior of different vertebrate species. When the composition comprising the INTEROMONE® is applied to or is released in the vicinity of different vertebrate species, the animal is calmed for a period of time. 2-methylbut-2-enal (as disclosed in U.S. application Ser. No. 13/623,279, filed on Sep. 20, 2012) is an example that works in a cross-species manner. Quinoline is another INTEROMONE® which is emitted in boar saliva and which can modify the behavior of different vertebrate species.

Formulations

The formulations of the present embodiments may comprise a chemical that is naturally secreted (exclusively in boar saliva), isolated from such a secretion, or synthetically duplicated from a vertebrate species. The chemicals that may be used, in accordance with the present invention, are those that produce a certain effect within the species from which they are secreted and a different effect when used in another species.

Figure 1:
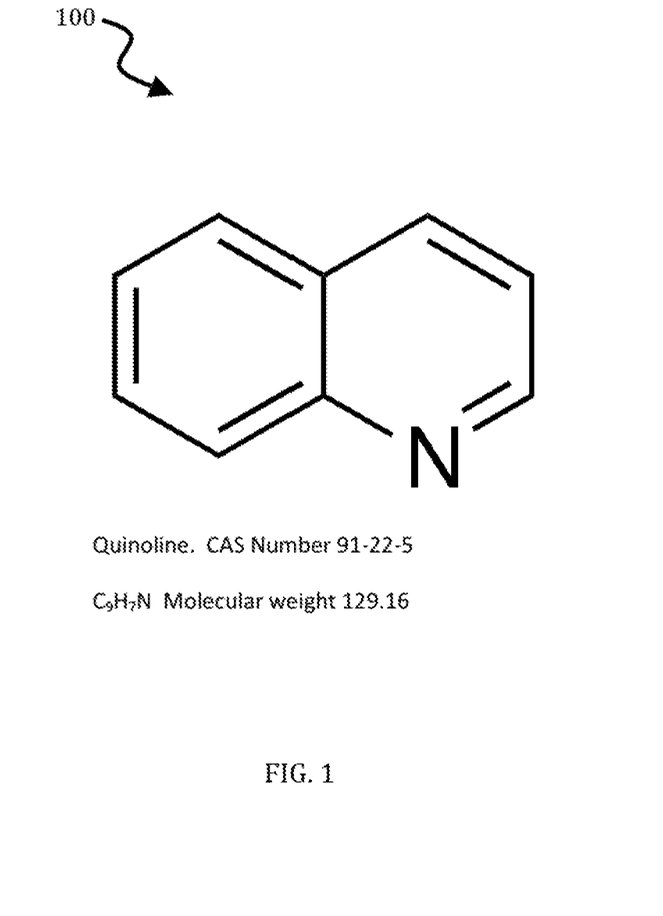
FIG. 1 depicts a structural formula for Quinoline in accordance with the disclosed embodiments.

The formulations of the present embodiments comprise an INTEROMONE®. In a preferred embodiment, a separate pheromone isolated strictly from boar saliva called Quinoline is used as an INTEROMONE®. The Quinoline used in the compositions may be the natural pheromone secreted or isolated directly from a boar, or a synthesized compound characterized by the structural formula 100, illustrated in FIG. 1.

Figure 2:
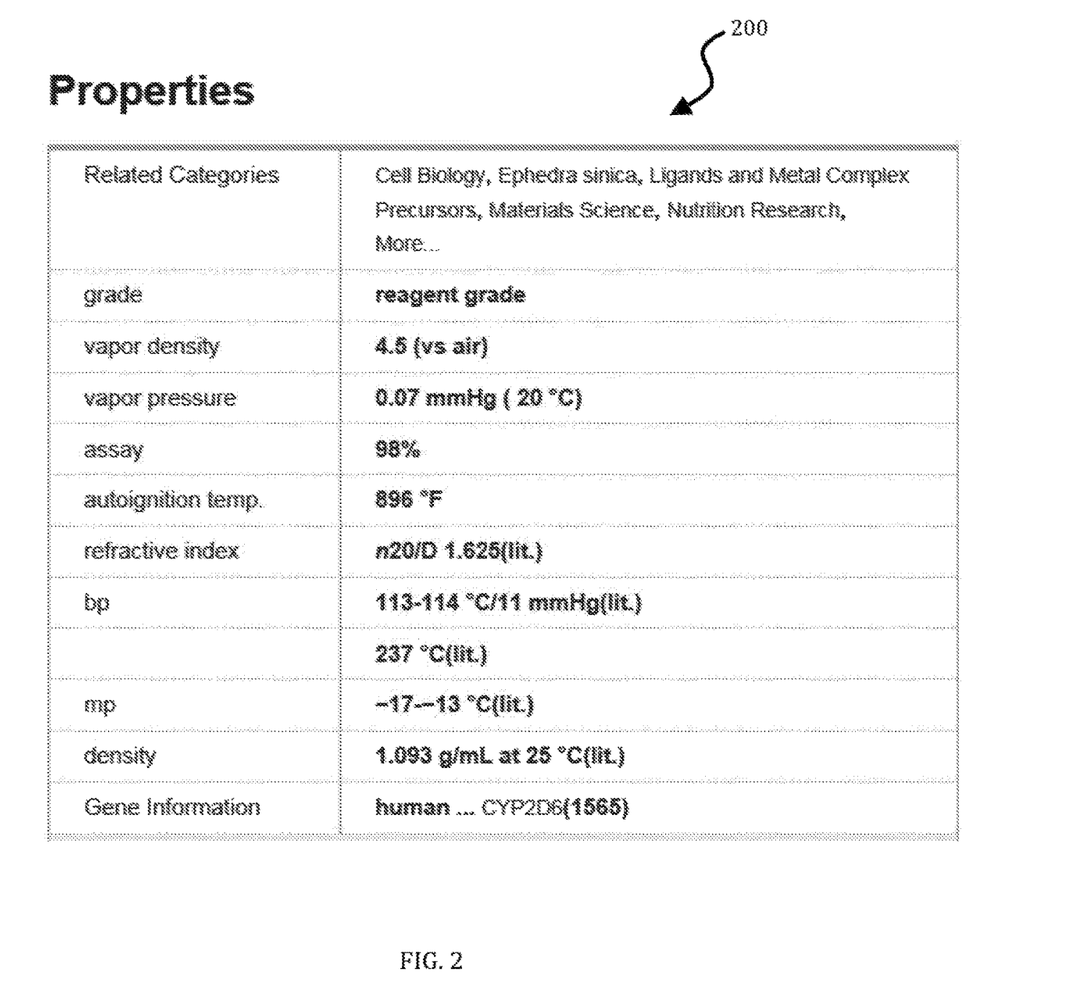
FIG. 2 depicts a property chart of Quinoline in accordance with the disclosed embodiments.

Quinoline or related compounds can have a chemical formula $C_9H_7N$. Quinoline has a CAS Registry number of 91-22-5. Compounds related to Quinoline that could also be used in accordance with the present invention include, but are not limited to, Quinoline derivatives. FIG. 2 illustrates a chart of properties 200 associated with Quinoline.

The amount of Quinoline necessary for the formulation to be effective in positively modifying, or otherwise altering, the behavior (e.g., calming, reduce nervousness, or lower the heart rate) of a particular animal should be at least 0.0001% (w/w) of the total composition. In one embodiment, the concentration of Quinoline in the composition ranges from between about 0.001% to about 1% (w/w). In another embodiment, the concentration of Quinoline in the composition ranges from between about 0.01% to about 0.1% (w/w). Preferably, the concentration of Quinoline present in the composition ranges from between about 0.001% to about 0.05% (w/w) and most preferably the concentration of Quinoline in the composition is about 0.01% (w/w).

In one embodiment, the composition of the present invention contains Quinoline. In other embodiments, the composition can contain a combination of Quinoline and at least one additional pheromone composition.

In addition to an INTEROMONE® comprising Quinoline, the formulations may optionally contain additional components such as solvents, propellants, surface-active agents, thickeners, and fragrances (i.e., "additional components"). The formulation may include one additional component or a combination of any of the forgoing additional components in varying amounts.

In an embodiment, the formulation includes at least one carrier solvent. Suitable carrier solvents are generally known within the art and are recognized to include lipophilic organic diluents, alcohols, ethylene glycol, propylene glycol, dipropylene glycol, ether, chloroform, benzene, carbon disulfide, oils including non-volatile and volatile liquids and oils, water, and combinations thereof. For example, an INTEROMONE® comprising Quinoline can be dissolved in a suitable alcohol and supplied in a liquid form such as a pump spray or for use in a plug-in diffuser. Suitable alcohols include ethanol, propanol, isopropanol, butanol, pentanol, hexanol, heptanol, octanol, and phenyl ethyl alcohol. In a preferred embodiment, the alcohols comprise ethanol, isopropanol, butanol, and phenyl ethyl alcohol. An alcohol solvent can be combined with water or a lipophilic organic diluent or carrier such as ethylene glycol, propylene glycol, dipropylene glycol, dipropylene glycol monoethyl ether, dipropylene glycol methyl ether, or Dow Corning® Q7-9180 silicone liquid. In a preferred embodiment, the solvent is a combination of water and an alcohol selected from the group consisting of ethanol or isopropanol.

In an embodiment, the amount of solvent present in the composition ranges from between about 0.5% and 99.99% (w/w) of the composition. Preferably, the amount of water present in the composition ranges from between about 70% and about 99.99% (w/w) of the composition and most preferably ranges from between about 80% and about 98.5% (w/w). Preferably the amount of alcohol present in the composition ranges from between about 1% and about 20% (w/w) and most preferably ranges from between about 1.5% and about 10% (w/w).

The formulation may additionally include a propellant. Suitable propellants include chlorofluorocarbons (CFC) such as trichloromonofluoromethane, dichlorodifluoromethane, and dichlorotetrafluoroethane; hydrochlorofluorocarbons (HCFC) or hydrofluorocarbons (HFC) such as chlorodifluoromethane, trifluoromonofluoroethane, chlorodifluoroethane, difluoroethane, and heptafluoropropane; hydrocarbons such as propane, butane, and isobutene; and compressed gases such as nitrogen, carbon dioxide, and nitrous oxide, as well as combinations of any of the above described propellants. In one embodiment, the propellant is propane. In another embodiment, the propellant is 1,1-difluoroethane. The propellant does not comprise an inert gas of Tumorigen compound class, which includes 1,1,1,2-tetrafluoroethane, chlorodifluoromethane, and dichlorodifluoromethane. Preferably, the propellant has a flash point of less than about −50 degrees C. Generally, when a propellant is included in the composition, such will range from between about 75% to about 99.99% (w/w) of the composition, preferably between about 85% and about 99.99% (w/w), and most preferably from between about 95% and about 99.99% (w/w).

The formulation may optionally include one or more surface-active agents (also called surfactants). Surfactants are generally used in preparing those embodiments of the directed to compositions that are formulated as emulsions. Either water in oil or oil in water emulsions may be formulated. Examples of suitable surfactants include: nonionic ethoxylated and nonethoxylated surfactants, abietic acid, almond oil PEG, beeswax, butylglucoside caprate, C18-C36 acid glycol ester, C9-C15 alkyl phosphate, caprylic/capric triglyceride PEG-4 esters, ceteareth-7, cetyl alcohol, cetyl phosphate, corn oil PEG esters, DEA-cetyl phosphate, dextrin laurate, dilaureth-7 citrate, dimyristyl phosphate, glycereth-17 cocoate, glyceryl erucate, glyceryl laurate, hydrogenated castor oil PEG esters, isosteareth-11 carboxylic acid, lecithin, lysolecithin, nonoxynol-9, octyldodeceth-20, palm glyceride, PEG diisostearate, PEG stearamine, poloxamines, polyglyceryls, potassium linoleate, PPG's, raffinose myristate, sodium caproyl lactylate, sodium caprylate, sodium cocoate, sodium isostearate, sodium tocopheryl phosphate, steareths, TEA-C12-C13 pareth-3 sulfate, tri-C12-C15 pareth-6 phosphate, and tridecetyls.

In certain applications, it may be desirable to increase the viscosity of the formulation. Suitable examples of thickening or viscosity increasing agents, include agents such as: acrylamides copolymer, agarose, amylopectin, bentonite, calcium alginate, calcium carboxymethyl cellulose, carbomer, carboxymethyl chitin, cellulose gum, dextrin, gelatin, hydrogenated tallow, hydroxyethylcellulose, hydroxypropylcellulose, hydroxypropyl starch, isopropyl palmitate, magnesium alginate, methylcellulose, microcrystalline cellulose, pectin, various PEG's, polyacrylic acid, polymethacrylic acid, polyvinyl alcohol, various PPG's, sodium acrylates copolymer, sodium carrageenan, xanthan gum, and yeast beta-glucan. The amount of thickener present in the formulation may range from between about 1% to about 30% (w/w), preferably from between about 5% to about 20% (w/w), and most preferably from between about 10% to about 15% (w/w).

The composition may additionally comprise a fragrance. The fragrance may be any fragrance that provides a desired odor masking effect since a particular INTEROMONE® may have a pungent odor. Although a variety of fragrances may be employed without departing from the scope of the present invention, suitable fragrances include floral essences, citrus blossoms, oil or extracts of conifers, or spices. Examples of floral essences include rose, lilac, lavender, gardenia, and jasmine. Suitable citrus blossoms include orange and lemon, and suitable oil or extracts of conifers include pine and juniper. Generally, fragrance may comprise between about 0.25% and about 1% (w/w) of the composition.

Routes of Administration

Mammals, including dogs, have several anatomical organs that receive olfactory signals. The two most dominant "smell" organs are the main olfactory epithelium (MOE) and the vomeronasal organ (VNO). Other sensory fibers are in the nasal cavity that can sense odors, but the main olfactory bulb and accessory olfactory bulb (receiving signals from the VNO) are the major integrating systems.

The olfactory bulb lies at the front of the brain. It sends neuronal projections through a bone and extends these projections into the olfactory epithelium. The MOE is an extensive area with a rich blood supply and mucosa in which odor aerosol molecules pass on their way to the lungs. Odor or water droplets will settle on the MOE, and if an odor receptor is present, that odor receptor will be bound and cause activation of the sensory neurons. Among all the genes in the mammalian body, the olfactory receptors have the largest number of genes. This indicates the importance of olfactory communication in animals, some of which seems to be lost in humans.

In certain embodiments, administration of the INTEROMONE® composition comprising Quinoline to a subject animal is accomplished through any method allowing for delivery of an effective amount of the INTEROMONE® via inhalation by the animal. Such methods of administration include, for example, placing or distributing the composition comprising the INTEROMONE® in the environment of the animal, either by incorporating the composition into a wearable device such as a collar, or by applying (e.g., spraying or wiping) the composition to surfaces in the living environment of the animal or directly onto the animal, such as to its facial region or head. For example, the INTEROMONE® composition may be administered topically to an animal using an aerosol, pump spray, foam, collar, wipe, dip, liquid, gel, lotion, and/or cream. The term "effective amount" describes an amount of INTEROMONE® present in a composition that is sufficient to produce a noticeable modification, i.e., improvement, of animal behavior in the subject animal, as determined according to behavioral observations as described herein. The effective amount will depend on factors such as the severity of the behavior being treated; individual animal parameters including age, physical condition, size and weight; concurrent treatments; the frequency of treatment; or the mode of administration. These factors are well known to those of ordinary skill in the art and can be addressed with no more than routine experimentation.

In one embodiment, the INTEROMONE® comprising Quinoline can be incorporated in various ways into a solid carrier material to form a collar or tag, and the collar or tag is then worn by the animal. The solid carrier material is selected from among those materials, typically polymeric compounds, generally recognized to be suitable for release of active compounds and set forth in further detail herein below. Alternatively, the INTEROMONE® can be combined with a solvent to form a liquid solution and the liquid solution can be further prepared in various formulations suitable for delivery to the animal by inhalation. For example, liquid solutions can be further prepared according to methods well known in the art such as a pump spray, aerosol, gel, foam, shampoo, dip, cream, lotion, gel, diffuser, or spot-on formulation.

In one embodiment, Quinoline is dissolved or diluted in a nonaqueous organic solvent or solvent mixture to form a solution for incorporation into a pump spray containing the INTEROMONE®. The solution may optionally be combined with at least one additional pheromone/INTEROMONE® or pheromone/INTEROMONE® composition. A preferred pump spray solution will comprise about 0.001% (w/w) Quinoline, about 10% (w/w) isopropyl alcohol, and about 89% (w/w) water. Additionally, between about 0.5% and 1% (w/w) of a fragrance may be added to the solution.

In another embodiment, Quinoline is dissolved or diluted with a solvent and combined with a propellant to form a solution for incorporation into an aerosol spray composition containing the INTEROMONE®. A preferred aerosol spray solution will comprise about 0.001% (w/w) Quinoline, about 2% (w/w) ethanol, and about 97% (w/w) propane. Additionally, between about 0.5% and 1% (w/w) of a fragrance may be added to the solution.

In yet another alternative embodiment, Quinoline is dissolved or diluted with a solvent and a thickener to form a solution for use in a diffuser. The solution may optionally be combined with at least one additional pheromone/INTEROMONE® or pheromone/INTEROMONE® composition. A preferred diffuser solution will comprise about 0.02% (w/w) Quinoline, between about 80% to about 85% (w/w) solvent, about 15% (w/w) thickener. Additionally, between about 0.25% and 1% (w/w) of a fragrance may be added to the solution.

In an additional embodiment, the INTEROMONE® may be incorporated into a solid carrier material to form a matrix composition containing the INTEROMONE® (or INTEROMONE® combined with at least one additional pheromone/INTEROMONE® or pheromone/INTEROMONE® composition), such as a fabric garment or a collar. The matrix containing the INTEROMONE® may be formed into a collar as is well known and amply described in the art, for example, in U.S. Pat. No. 3,852,416. Typically an admixture of an active (i.e., an INTEROMONE®) and a carrier material providing the matrix is formed into strips through an extrusion process, and each strip is then formed a collar by including a fastening device such as a buckle, snap, or hook. The solid carrier material forming the matrix into which the INTEROMONE® is incorporated is, for example, a polymer or polymer mixture with suitable release characteristics such that the pheromone is released from the collar to be inhaled by the animal. Additionally, the matrix containing the INTEROMONE® may be formed into a fabric garment as is described in the art, for example, in U.S. Publication No. 2010/0319632. The INTEROMONE® preferably contributes from between about 0.001% and about 1% (w/w), and preferably between about 0.01% and 0.5% (w/w) of the collar or fabric garment.

Suitable polymers for forming a solid substrate for making a collar are well known and include, but are not limited to, polyethylene, polyvinyl acetate, ethylene acid copolymers, ethylene acrylates, polyurethanes, styrene-butadiene, polyvinyl butyral, polyvinyl chloride (PVC), polyolefin, polyacrylate, and polymethacrylate esters, and silicon polymer. The polymers can contribute between about 50% to about 99.99% (w/w) of the collar, and typically will contribute between about 90% and about 99.99% (w/w) of the collar. Plasticizers can be incorporated into the mixture to render the polymer resin more flexible. Suitable plasticizers include phosphoric acid esters (e.g., tricresyl phosphate) or phthalic acid esters (such as dioctyl phthalate or diisodecyl phthalate (DIDP)). The collar may also include other additives such as stabilizers, for example, antioxidants to protect the collar material from degradation by UV light and other oxidizing factors. Lubricants, colorants, and fillers may also be included.

The present embodiments further include methods of using Quinoline in INTEROMONE® compositions to positively modify undesirable or inappropriate behaviors (e.g., barking, jumping, begging, and/or mobbing) or physiology in an animal by exposing the animal to an effective amount of an INTEROMONE®-based composition, wherein the composition comprises at least about 0.001% (w/w) of an INTEROMONE®. Generally, the composition comprises between about 0.001% and about 1% (w/w) of an INTEROMONE®.

Figure 4:
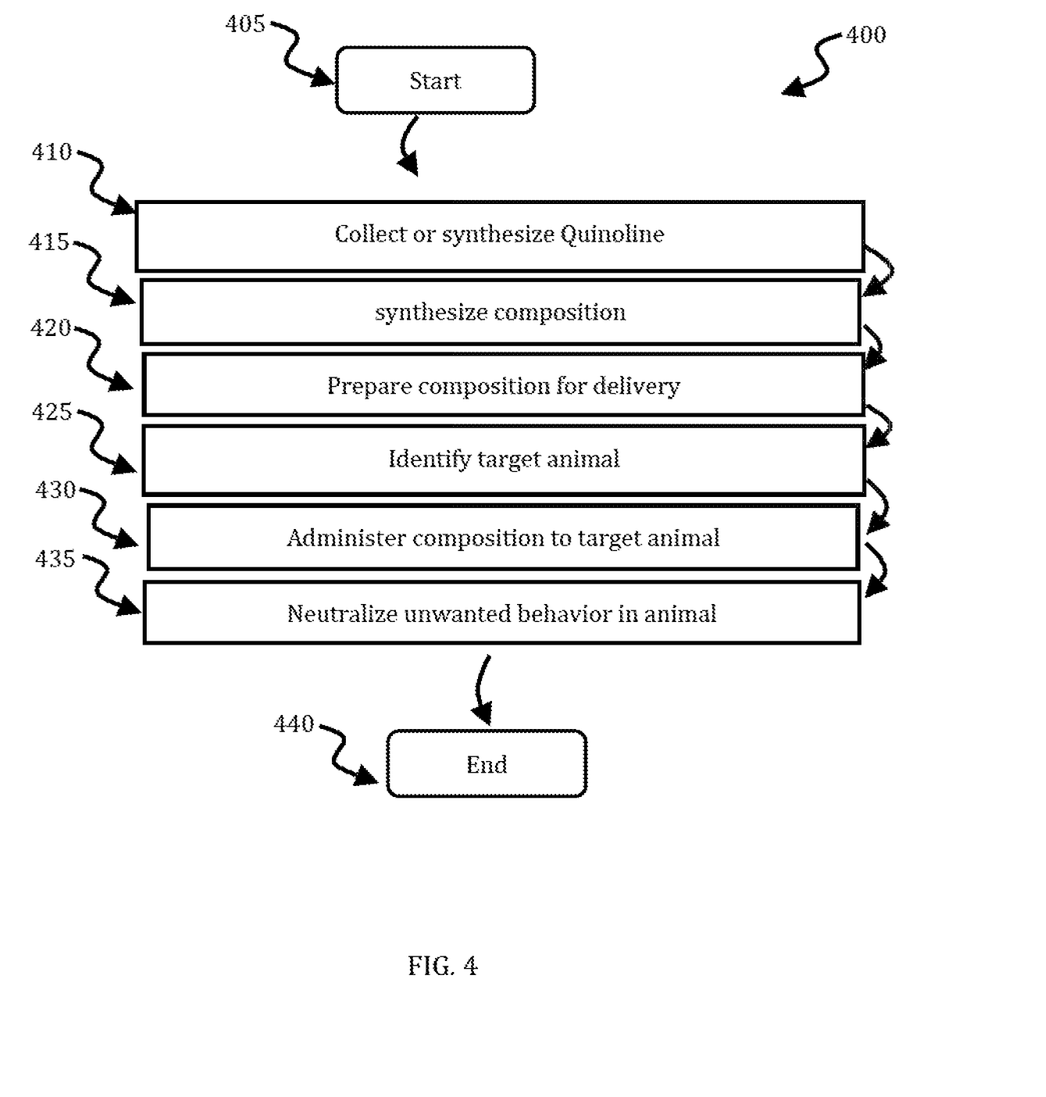
FIG. 4 depicts a flow chart of steps associated with a method to produce, or otherwise affect, behavior in a variety of vertebrate species, in accordance with an embodiment.

An exemplary method 400, illustrated in FIG. 4, starts at block 405. Quinoline can be collected from a boar or synthetically synthesized as illustrated at block 410. A composition including Quinoline and a carrier solvent can then be created as shown at block 415. At block 420, the composition can be prepared for delivery, preferably via inhalation although other means of delivery are also possible. Once the composition is prepared, an unruly animal displaying an unwanted behavior can be identified, as shown at block 425. The composition can then be administered to the animal, as illustrated at block 430 in order to neutralize the unwanted behavior, as shown at block 435. The method ends at block 440.

In another embodiment, an INTEROMONE® can first be configured. Next, the animal can be exposed to the composition by any method allowing inhalation by the animal over a period of time sufficient to effect a modification of the target behavior, as determined according to behavioral observations. Typically, depending on the chosen route of administration, the particular animal, and situation, the exposure of the composition to the animal will be over a period of at least one second, but can also be for a period of at least one hour, for a period between one hour and five hours, for a period of at least one day, for a period of at least one week, for a period of between one week and four weeks, for a period of at least one month, or for any period of time as may be needed to achieve a satisfactory behavioral effect.

For example, an animal suffering from a temporarily induced anxiety (e.g., a trip to a veterinary office, being handled, or fireworks) may require a brief exposure to the composition before, during, or after the anxiety-inducing event to relieve the anxiety and associated behavior. In contrast, an animal exposed to a stressful stimulus for a longer and continual period, such as a pet exposed to a new pet in the household, may benefit from regular exposure to the INTEROMONE® composition for an extended period.

Commonly recognized sources of stress in animals include, for example, weaning, transportation (especially in motorized vehicles), boredom, lack of exercise, separation anxiety, loud noises, events that induce barking/jumping/ begging or anxiety, introduction to new people or animals, and visits to a veterinary office. Animals that are stressed by exposure to such events or conditions will typically exhibit highly undesirable stress-related behavioral symptoms. Such undesirable behaviors are commonly recognized and include, for example, fearful behavior such as cowering or shaking; excessive chewing, barking, begging, pacing, or excessive laying down; hyperactivity such as jumping; aggressive behavior toward people or other animals such as growling, snappishness, or biting; property destruction; and frequent urination or soiling. When undesirable behaviors are observed, the composition of the present embodiments may be used to induce a temporary state of lower activity, calm, and reduced excitability.

In use, the composition of Quinoline comprising an INTEROMONE® can be implemented in a number of different ways depending in part on the targeted animals and behavior desired to be modified. A liquid solution containing an INTEROMONE® can simply be applied directly to the coat or skin of the animal, or sprayed on surfaces or objects in the animal's environment, or diffused or sprayed into the air in the animal's environment. For example, an exemplary liquid spray formulation containing Quinoline (dissolved in a suitable solvent) can be sprayed, for example, on the animal's nostrils, face, or head, or in its environment such that it may be perceived through olfaction as frequently as needed to obtain the desired behavioral modification. Alternatively, an INTEROMONE® in liquid, gas, or solid form can be incorporated in a plasticized material such as PVC or the like that can then be formed into a tag or in strips to form a collar. Furthermore, the INTEROMONE® composition can be combined with at least one additional pheromone/ INTEROMONE® or pheromone/INTEROMONE® composition (natural or synthetic) prior to implementation into any of the above-mentioned modes of delivery to the animal.

It should be understood that the INTEROMONE® used in the composition may be provided in the form of pure concentrate Quinoline (100% concentration) or a diluted composition with additional excipients in the dosage form (i.e., the amount of active ingredient in the composition is less than or equal to 99.99%, and the remainder consists of inactive excipients). If diluted, the amount of Quinoline dispensed in the various dosage forms may range from between about 1.0 pg/mL to about 1.0 g/mL, more preferably between about 1.0 ng/mL to about 1.0 g/mL. One skilled in the art will appreciate that the volume of active component added to the composition will need to be adjusted to account for the dilution and to ensure the end composition comprises the appropriate final concentration of INTEROMONE®. One skilled in the art will also appreciate that the various components of the composition may be provided in a variety of dosage forms including, but not limited to liquid solution or suspension, emulsion, aerosol, slow release matrices, and the like.

The compositions according to the embodiments may be applied in a variety of ways, but are best applied by exposing the olfactory system by any means such as, for example, spraying a light mist directly on the facial region or in the environment of the animal whose behavior is intended to be modified. Further, the methods of the current invention are best accomplished by allowing the animal to inhale the composition, as the nasal cavities, sinuses, lungs and throats of animals present a large area for the aromatic molecules to be bound to an olfactory receptor. The application of the composition to the animal or the animal's environment may be repeated as often as necessary to modify the animal's behavior.

The efficacy of Quinoline was tested in three studies conducted to determine if Quinoline would reduce dog barking and jumping. The composition used in the experiments comprised approximately 4 micrograms per milliliter of Quinoline.

Figure 3:
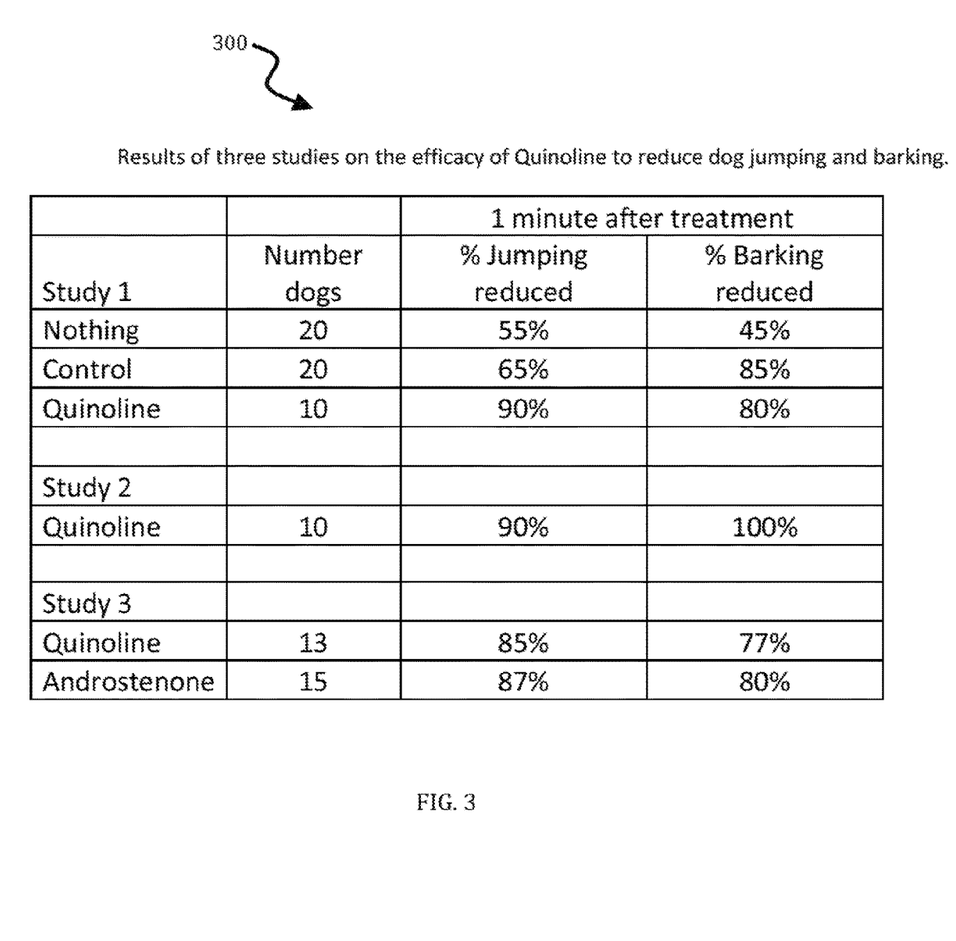
FIG. 3 depicts a table of study results, in accordance with the disclosed embodiments.

The basic parameters of the test involved walking a teaser dog in the center aisle of a dog kennel with test dogs on either side in kennels. The kennels were chain-linked fence with concrete floors. The researchers walked a teaser dog down the aisle and recorded dogs jumping and barking over a two minute period. The data from the tests is summarized in Table 300, illustrated in FIG. 3, which his indicative of the first minute after treatment.

Study 1

In the first study, three treatments were evaluated. Treatment 1 represented no treatment of any kind. The teaser animal simply stood at the test subjects' kennel. About half the test subjects naturally stopped jumping and barking during treatment 1.

Treatment 2 represented a control treatment. In this case, the delivery vehicle (isopropyl alcohol) spray was administered without Quinoline. In the control test, jumping and barking was reduced as compared to treatment 1.

In treatment 3, Quinoline was administered to the test subject animals. Administration of the Quinoline in treatment 3 reduced jumping by 90% and barking by 80%. These results suggest Quinoline is effective in reducing unwanted jumping and barking in dogs.

Study 2

In study 2, the efficacy of Quinoline alone was tested. Test 2 was conducted a week after test 1. The same procedure was used in study 2 except that the test animals were only subject to the delivery of Quinoline. In study 2, the administration of Quinoline reduced jumping by 90% and barking by 100%. Comparing the results of study 2 to treatment 1 and treatment 2 in study 1, again, indicates the efficacy of Quinoline in reducing unwanted jumping and barking in dogs.

Study 3

In study 3, Quinoline was compared to Androstenone (the compound described in U.S. Pat. No. 9,044,395). Again, the same procedures were used in study 3; the test animals were subject to Quinoline and Androstenone. Study 3 suggests that Quinoline and Androstenone are approximately equivalently effective in reducing barking and jumping.

It is important to note that while the efficacy of Quinoline and Androstenone is approximately equivalent, Quinoline is a wholly different compound from Androstenone. In particular, Quinoline is a heterocyclic aromatic organic compound with the chemical formula $C_9H_7N$. Quinoline is prevalent in a variety of pharmacologically active synthetic and natural compounds and can have antiseptic, antipyretic, and antiperiodic properties. Quinoline is a catabolite of tryptophan, a fundamental structure in some antihypertensive agents such as the epripheral vasodilators prazosin and doxazosin.

Based on the foregoing, it can be appreciated that a number of embodiments, preferred and alternative, are disclosed herein. It will be appreciated that variations of the above-disclosed and other features and functions, or alternatives thereof, may be desirably combined into many other different systems or applications. For example, in an embodiment, a composition for reducing unwanted behavior in mammals comprises a combination of Quinoline and at least one delivery compound. The composition can comprise the chemical 100 illustrated in FIG. 1. In an embodiment, the delivery compound further comprises a propellant.

In an embodiment, the composition further comprises a carrier solvent. In an embodiment, the carrier solvent is selected from the group comprising: lipophilic organic diluents, alcohols, ethylene glycol, propylene glycol, dipropylene glycol, ether, chloroform, benzene, carbon disulfide, oils including non-volatile and volatile liquids and oils, water, and combinations thereof.

In another embodiment, the alcohol is selected from the group comprising: ethanol, propanol, isopropanol, butanol, pentanol, hexanol, heptanol, octanol, phenyl ethyl alcohol, and combinations thereof.

In another embodiment, the composition is formulated as at least one of: a spray, an aerosol composition, a diffuser, and a slow release matrix.

In another embodiment, Quinoline is present in an amount from between about 0.0001% to about 1% (w/w) of the composition.

In yet another embodiment, a method of modifying behavior in an animal comprises administering a composition to the animal, the composition comprising Quinoline and at least one carrier solvent. In an embodiment, the animal is selected from the group comprising: a dog, a cat, and a horse. In another embodiment of the method, the composition further comprises a propellant. In an embodiment, the administration comprises inhalation.

In another embodiment of the method, the composition is formulated as at least one of: a spray, an aerosol, a diffuser, and a slow release matrix.

In an embodiment of the method, administration further comprises at least one of: spraying the animal with the composition and spraying an environment surrounding the animal with the composition. In an embodiment, the period of exposure time is at least one second.

In another embodiment of the method, the composition comprises synthetically created Quinoline. The composition can comprise 0.01% (w/w) Quinoline, 2.0% (w/w) ethanol, and 97.99% (w/w) propane. In another embodiment, the composition comprises 0.01% (w/w) synthetic Quinoline, 2.0% (w/w) ethanol, and 97.99% (w/w) propane. In another embodiment, the composition comprises 0.01% (w/w) Quinoline, 10.0% (w/w) isopropyl alcohol, 89.49% (w/w) water, and 0.5% (w/w) fragrance.

In another embodiment, a method of modifying behavior in a dog comprises administering a pheromone composition to the dog, the composition comprising between 0.0001% and 1% (w/w) of Quinoline, and between about 0.5% and 99.99% (w/w) of at least one carrier solvent, wherein the amount of Quinoline administered to the dog is between about 1.0 pg/mL to about 1.0 g/mL.

Various presently unforeseen or unanticipated alternatives, modifications, variations or improvements therein may be subsequently made by those skilled in the art which are also intended to be encompassed by the following claims.

What is claimed is:

1. A composition for reducing unwanted behavior in mammals, the composition comprising:
    a combination of Quinoline and at least one delivery compound, the at least one delivery compound comprising an alcohol, wherein said Quinoline is present in an amount from between 0.0001% and 1% (w/w) of the composition;
    a propellant comprising at least one of a chlorofluorocarbon and a compressed gas;
    a surface-active agent; and
    a fragrance.

2. The composition of claim 1, wherein Quinoline comprises:
    synthetically created Quinoline.

3. The composition of claim 1 wherein the alcohol comprises phenyl ethyl alcohol.

4. The composition of claim 1 wherein the composition further comprises a carrier solvent, the carrier solvent comprising the alcohol mixed with at least one of:
- lipophilic organic diluents;
- ethylene glycol;
- propylene glycol;
- dipropylene glycol; and
- combinations thereof.

5. The composition of claim 1 wherein the alcohol is selected from the group comprising:
- ethanol;
- propanol;
- butanol;
- pentanol;
- hexanol;
- heptanol;
- octanol; and
- combinations thereof.

6. The composition of claim 1, wherein the composition is formulated as at least one of:
- a spray;
- an aerosol composition;
- a diffuser; and
- a slow release matrix.

\* \* \* \* \*